(12) United States Patent
Furuhata

(10) Patent No.: US 10,866,729 B2
(45) Date of Patent: Dec. 15, 2020

(54) TOUCH PANEL DEVICE, BENDING CONTROL PROGRAM, RECORDING MEDIUM INCLUDING BENDING CONTROL PROGRAM RECORDED THEREIN, AND ENDOSCOPE BENDING CONTROL METHOD

(71) Applicant: Olympus Corporation, Hachioji (JP)

(72) Inventor: Tsuyoshi Furuhata, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/283,925

(22) Filed: Feb. 25, 2019

(65) Prior Publication Data
US 2019/0303000 A1    Oct. 3, 2019

(30) Foreign Application Priority Data
Mar. 29, 2018   (JP) .................... 2018-064865

(51) Int. Cl.
| | | |
|---|---|---|
| *G06F 3/041* | (2006.01) | |
| *G06F 3/0488* | (2013.01) | |
| *A61B 1/00* | (2006.01) | |
| *A61B 1/005* | (2006.01) | |
| *G06F 3/0482* | (2013.01) | |

(52) U.S. Cl.
CPC ...... *G06F 3/04886* (2013.01); *A61B 1/00039* (2013.01); *A61B 1/00045* (2013.01); *A61B 1/0051* (2013.01); *G06F 3/041* (2013.01); *G06F 3/0482* (2013.01); *G06F 2203/04803* (2013.01)

(58) Field of Classification Search
CPC ............... G06F 3/04886; G06F 3/041; G06F 2203/04803; G06F 3/0482; A61B 1/00045; A61B 1/0051; A61B 1/00039; A61B 1/0005; A61B 1/0052
See application file for complete search history.

(56) References Cited

U.S. PATENT DOCUMENTS

| | | | | |
|---|---|---|---|---|
| 8,813,100 | B1 * | 8/2014 | Platzer .................. | G06F 3/0485 719/328 |
| 2006/0015012 | A1 * | 1/2006 | Sato .................... | A61B 1/00039 600/118 |
| 2010/0083190 | A1 * | 4/2010 | Roberts ............... | G06F 3/04883 715/863 |
| 2010/0251181 | A1 * | 9/2010 | Lal ..................... | H04N 1/00347 715/834 |
| 2012/0124520 | A1 * | 5/2012 | Samp .................. | G06F 3/04886 715/834 |

FOREIGN PATENT DOCUMENTS

JP        2005-052635        3/2005

* cited by examiner

*Primary Examiner* — Carolyn R Edwards
(74) *Attorney, Agent, or Firm* — Scully, Scott, Murphy & Presser, P.C.

(57) ABSTRACT

The disclosed technology is directed to a touch panel device used in an endoscope device. The touch panel device includes a display portion having a display panel and a touch panel formed thereto and configured to display an endoscope image on the display panel acquired by an endoscope having a bending portion. A processor is configured to control the bending portion so as to perform a bending operation when a user keeps performing a first operation on the touch panel in a first predetermined duration or more.

18 Claims, 12 Drawing Sheets

TOUCH PANEL DEVICE, BENDING CONTROL PROGRAM, RECORDING MEDIUM INCLUDING BENDING CONTROL PROGRAM RECORDED THEREIN, AND ENDOSCOPE BENDING CONTROL METHOD

CROSS-REFERENCE TO RELATED APPLICATION

This application is a Non-provisional application which claim priority to the Japanese Patent Application No. 2018-064865 filed in the Japan Patent Office on Mar. 29, 2018, which is hereby incorporated by reference in its entirety.

TECHNICAL FIELD

The disclosed technology relates to a touch panel device, a bending control program, a recording medium including the bending control program recorded therein, and an endoscope bending control method.

DESCRIPTION OF THE RELATED ART

A known endoscope device displays, on a monitor, an endoscope image of inside of an object taken using an insertion portion inserted into the object. For example, Japanese Patent Laid-Open No. 2005-52635 discloses an endoscope device displaying an endoscope image and a manipulation image on a monitor. In this endoscope device, a bending portion of an insertion portion of the endoscope displayed on the manipulation image is manipulated by operating a keyboard or mouse. A distal end portion of the insertion portion is directed toward the object according to an input of bending instruction and images the object. An endoscope image resulting from the imaging is displayed on the monitor.

Another known example is a touch panel allowing various instructions to be input by touch panel operation on a displayed image. The touch panel may be used to input various instructions for the endoscope device.

BRIEF SUMMARY OF EMBODIMENTS

However, the known endoscope device has disadvantages. For example, a manipulation image may be displayed on the touch panel, so that the bending portion of the insertion portion can be manipulated by performing touch panel operation on the manipulation image. In such a case, when a user bends the insertion portion, the user's eyes shift from the endoscope image to the manipulation image to allow the position of the manipulation image to be checked. Achieving accurate manipulation while gazing the endoscope image is thus difficult.

An object of the disclosed technology is thus to provide a touch panel device, a bending control program, a recording medium including the bending control program recorded therein, and an endoscope bending control method, all of which allow the bending portion of the insertion portion to be more accurately manipulated with no need to shift the user's eyes to the manipulation image and with the user's eyes fixed at the endoscope image.

A touch panel device according to an aspect of the disclosed technology includes a display portion including a touch panel and configured to display a display screen including an endoscope image acquired by an endoscope with a bending portion, and a control portion configured to controllably cause the bending portion to perform a bending operation when a first operation lasting a predetermined duration or more from touch start until touch end is performed on the display screen.

A bending control program according to an aspect of the disclosed technology causes a computer to execute a code displaying, on a display portion with a touch panel, a display screen including an endoscope image acquired by an endoscope with a bending portion, and a code controllably causing the bending portion to perform a bending operation when a first operation lasting a predetermined duration or more from touch start until touch end is performed on the display screen.

A recording medium according to an aspect of the disclosed technology includes a bending control program recorded therein, the bending control program causing a computer to execute a code displaying, on a display portion with a touch panel, a display screen including an endoscope image acquired by an endoscope with a bending portion, and a code controllably causing the bending portion to perform a bending operation when a first operation lasting a predetermined duration or more from touch start until touch end is performed on the display screen.

An endoscope bending control method according to an aspect of the disclosed technology includes preparing a display portion with a touch panel displaying a display screen, displaying, on the display portion, the display screen including an endoscope image acquired by an endoscope with a bending portion, and controllably causing the bending portion to perform a bending operation when a first operation lasting a predetermined duration or more from touch start until touch end is performed on the display screen.

The disclosed technology can provide a touch panel device, a bending control program, a recording medium including the bending control program recorded therein, and an endoscope bending control method, all of which allow the bending portion of the insertion portion to be more accurately manipulated with no need to shift the user's eyes to the manipulation image and with the user's eyes fixed at the endoscope image.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Embodiments of the disclosed technology will be described below with reference to the drawings.

Configuration of First Embodiment

Figure 1:
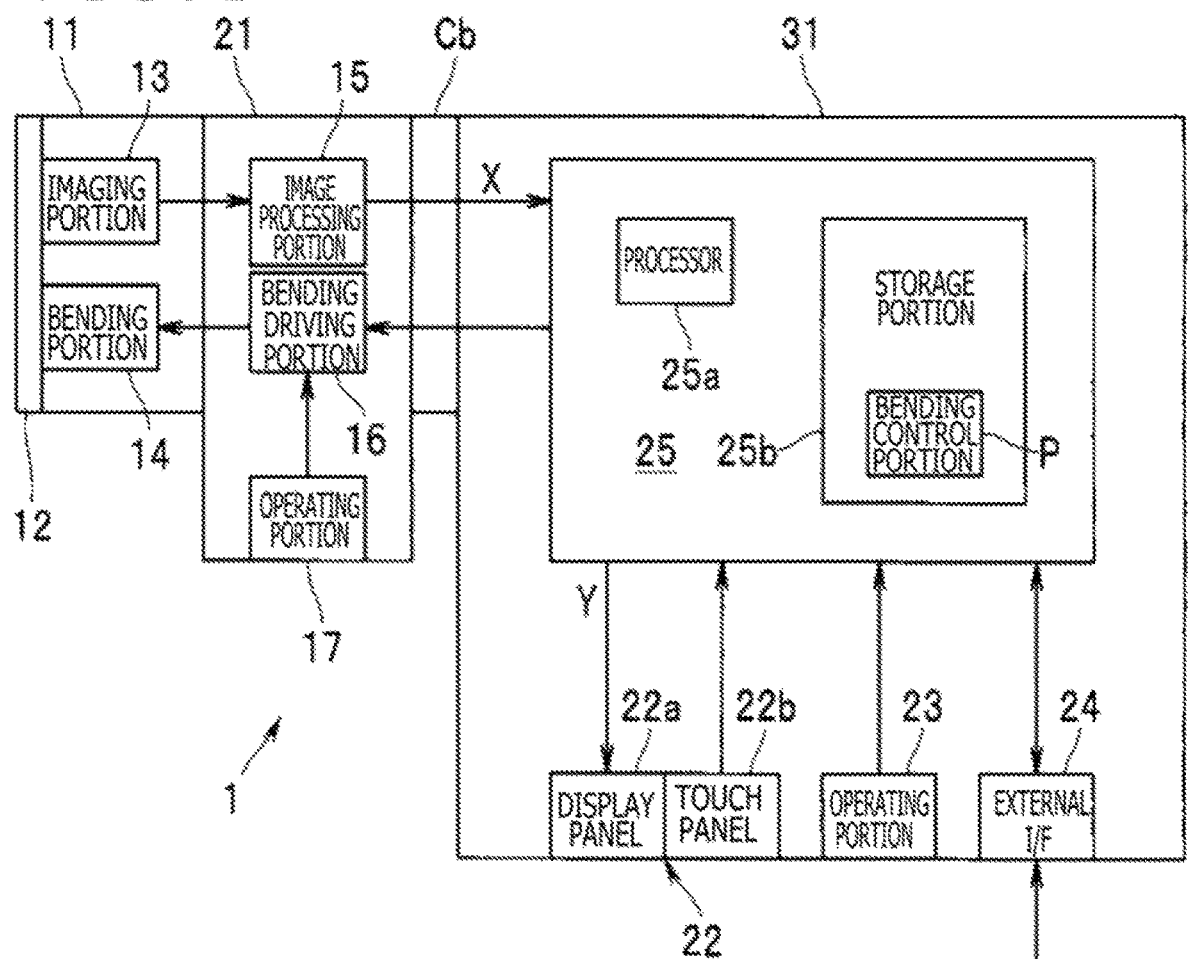
FIG. 1 is a block diagram illustrating an example of a configuration of a touch panel device according to a first embodiment of the disclosed technology.
Figure 1:
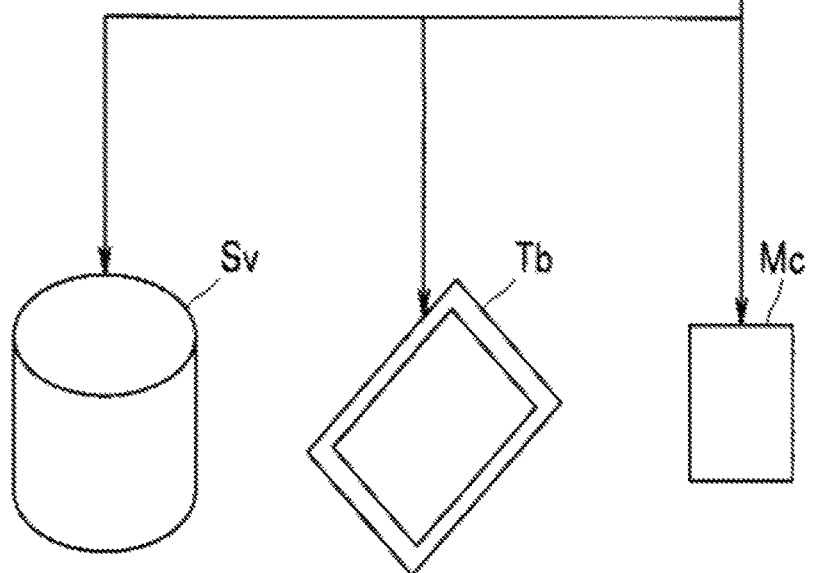

FIG. 1 is a block diagram illustrating an example of a configuration of a touch panel device 31 according to a first embodiment of the disclosed technology.

An endoscope device 1 includes an insertion portion 11, an endoscope 21, and the touch panel device 31.

The insertion portion 11 has an elongate shape enabling the insertion portion 11 to be inserted into an object. The insertion portion 11 includes an optical adapter 12, an imaging portion 13, and a bending portion 14.

The optical adapter 12 is installed at a distal end portion of the insertion portion 11. The optical adapter 12 is replaceable depending on the object. The optical adapter 12 includes an observation window and an optical system to project return light from the object on the imaging portion 13.

The imaging portion 13 is disposed at the distal end portion of the insertion portion 11. The imaging portion 13 includes an imaging element including a complementary metal-oxide semiconductor (CMOS) or a charge-coupled device (CCD) to image the object. The imaging portion 13 converts an object image input via the optical adapter 12 into an imaging signal to output the imaging signal to the endoscope 21.

The bending portion 14 is disposed at a proximal end side of the imaging portion 13 and bent under the control of the endoscope 21.

The insertion portion 11 may include a lighting portion (not illustrated) at the distal end portion thereof to light the object.

The endoscope 21 is attached to the distal end portion of the insertion portion 11. The endoscope 21 includes an image processing portion 15, a bending driving portion 16, and an operating portion 17.

The image processing portion 15 executes image processing on an imaging signal input from the imaging portion 13 to generate an endoscope image X. The image processing portion 15 then outputs the endoscope image X to the touch panel device 31.

The bending driving portion 16 is coupled to the bending portion 14 by a plurality of pulling members that bend the bending portion 14. The bending driving portion 16 pulls the pulling members to bend the bending portion 14 in a direction corresponding to a bending instruction input from the touch panel device 31.

For example, when a bending instruction instructing upward bending is input, the bending driving portion 16 pulls an upward-bending pulling member to bend the bending portion 14 upward such that the distal end portion of the insertion portion 11 is bent upward with respect to an insertion direction. Similarly, when a bending instruction instructing downward bending, leftward bending, or rightward bending is input, the bending driving portion 16 bends the bending portion 14 downward, leftward, or rightward according to the bending instruction.

The bending driving portion 16 also pulls, by a predetermined pulling amount, two of the pulling members for bending the bending portion 14 in different directions. The bending driving portion 16 can thus cause bending of the bending portion 14 in a desired direction other than the four directions, for example, upward and leftward bending, downward and leftward bending, upward and rightward bending, and downward and rightward bending.

The bending driving portion 16 can further bend the bending portion 14 so as to rotate the distal end portion of the insertion portion 11 around the bending portion 14, according to the bending instruction from the touch panel device 31.

The operating portion 17 includes operating tools such as a freeze button, a release button, a joystick, a zoom button, and a menu button. A user operates the operating portion 17 to input various instructions.

The touch panel device 31 is connected to the endoscope 21 by a cable Cb. The touch panel device 31 includes a display portion 22, an operating portion 23, an external I/F 24, and a control portion 25. The touch panel device 31 may be configured integrally with the endoscope 21.

The display portion 22 includes a display panel 22a and a touch panel 22b.

The display panel 22a includes, for example, a liquid crystal display (LCD) or an organic light emitting diode (OLED) to display a display screen Y input from the control portion 25.

The touch panel 22b is disposed in superimposition with the display panel 22a to output input of the user's various instructions thereon to the control portion 25.

The operating portion 23 includes operating tools such as a freeze button, a release button, a joy stick, a zoom button, and a menu button.

The external I/F 24 is a circuit for external connection. The endoscope device 1 can be connected, by the external I/F 24, to an external storage device such as a memory card Mc. The endoscope device 1 also performs by wired or wireless communication using the external I/F 24. The endoscope device 1 can be connected, via a network, to a tablet terminal Tb or to an external terminal device such as a server Sv.

The control portion 25 controls operation of each of the portions in the endoscope device 1. The control portion 25 includes a processor 25a and a storage portion 25b. The control portion 25 generates, based on the endoscope image X input from the image processing portion 15, the display screen Y to be displayed on the display portion 22. The control portion 25 outputs the display screen Y to the display portion 22.

The processor 25a can execute various programs loaded from the storage portion 25b, the external storage device, or the external terminal device. Functions of the control portion 25 are implemented by the processor 25a by executing the corresponding programs. Furthermore, some or all of the functions of the control portion 25 may be configured using, for example, a circuit with a field programmable gate array (FPGA) or an application specific integrated circuit (ASIC).

The storage portion 25b includes a rewritable storage element such as a random access memory (RAM), a read only memory (ROM), or a flash memory. The storage portion 25b stores programs and data used to control operation of each of the portions in the endoscope device 1.

A bending control portion P is also stored in the storage portion 25b. The bending control portion P includes codes of a bending control process for controlling the bending driving portion 16 according to instructions input via the touch panel 22b.

Configuration of Display Screen Y

A configuration of the display screen Y displayed on the display portion 22 will now be described.

Figure 2:
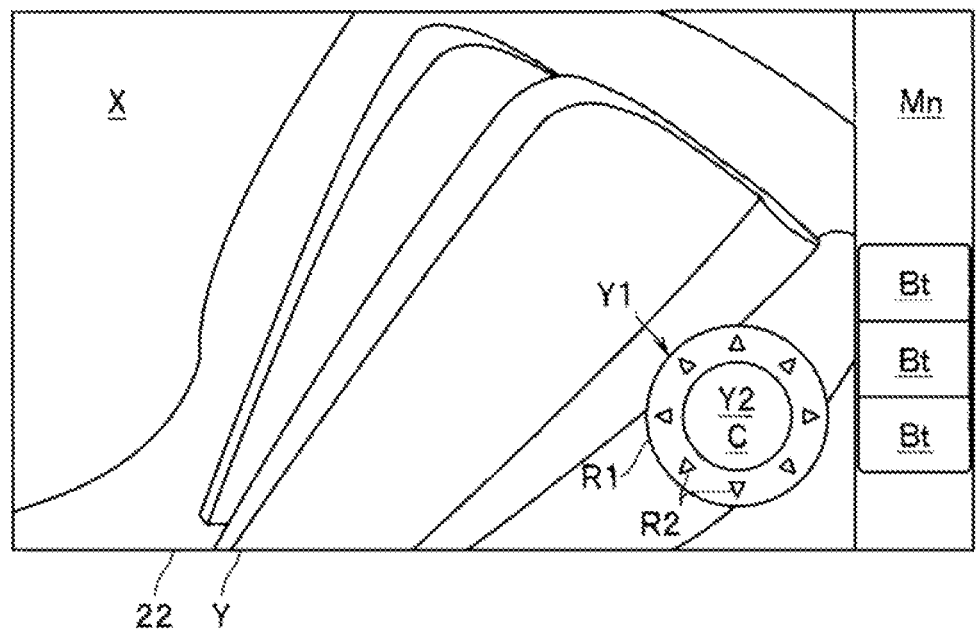
FIG. 2 is a diagram illustrating an example of a display screen displayed on a display portion of a touch panel device according to the first embodiment of the disclosed technology.
Figure 3:
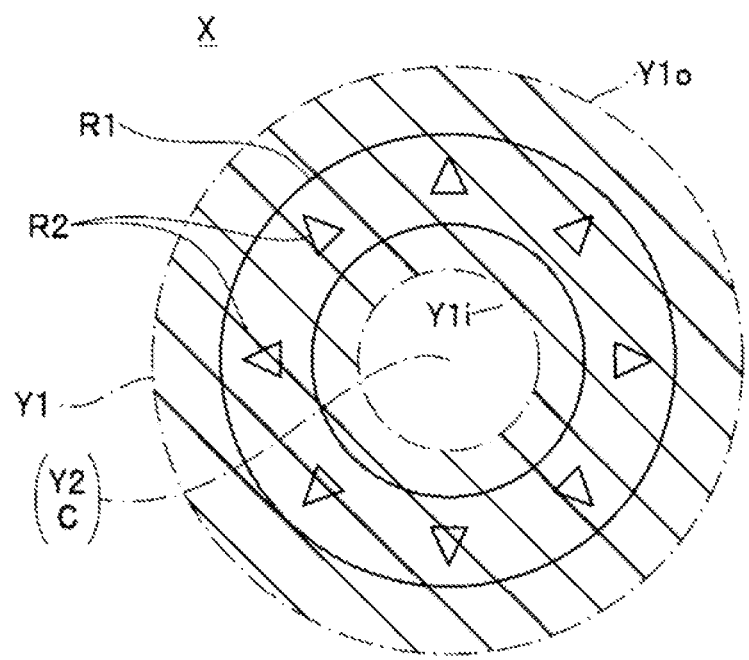
FIG. 3 is a diagram illustrating a bending instruction area and a bending stop area of the touch panel device according to the first embodiment of the disclosed technology.
Figure 4:
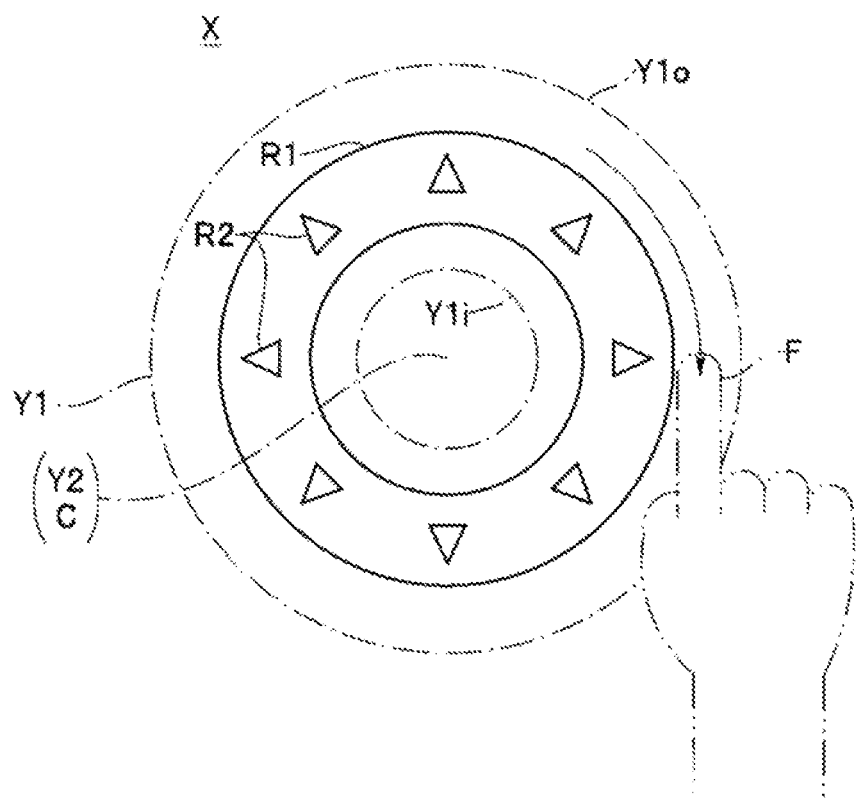
FIG. 4 is a diagram illustrating the bending instruction area and the bending stop area of the touch panel device according to the first embodiment of the disclosed technology.
Figure 5:
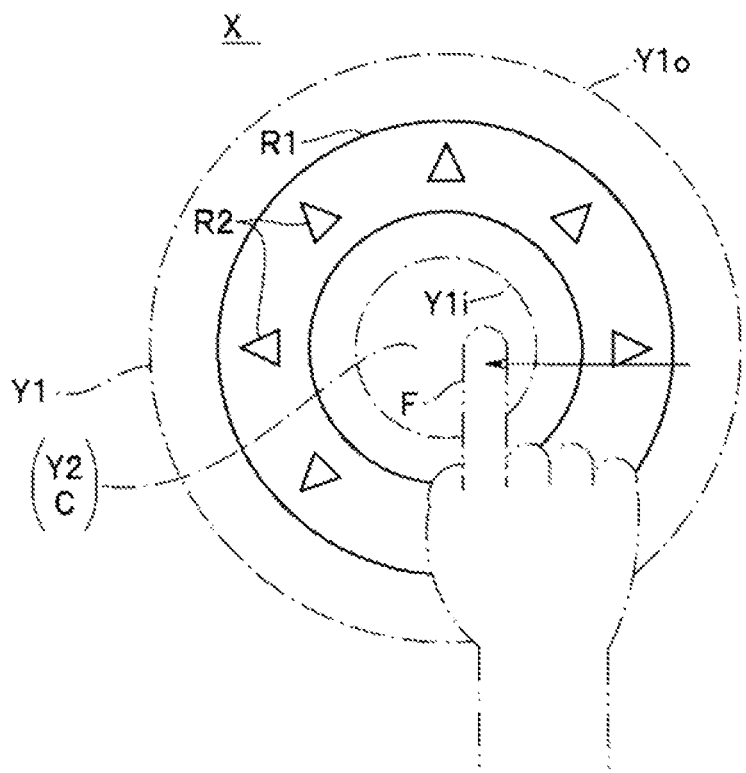
FIG. 5 is a diagram illustrating the bending instruction area and the bending stop area of the touch panel device according to the first embodiment of the disclosed technology.

FIG. 2 is a diagram illustrating an example of the display screen Y displayed on the display portion 22 of the touch panel device 31 according to the first embodiment of the disclosed technology. FIGS. 3 to 5 are diagrams illustrating a bending instruction area Y1 and a bending stop area Y2 of the touch panel device 31 according to the first embodiment of the disclosed technology.

On the display screen Y, instructions can be input by a first operation and a second operation.

The first operation is an operation performed by keeping the user's finger F in touch with the touch panel 22b for a predetermined duration or more. The first operation includes a swipe operation of sliding the finger F on the touch panel 22b and a long tap operation of keeping in touch with the touch panel 22b at one point.

The second operation is an operation performed by putting the user's finger F in touch with the touch panel 22b for less than the predetermined duration. The second operation includes a tap operation of tapping the touch panel 22b with the finger F.

As illustrated in FIG. 2, the display screen Y includes the endoscope image X, the bending instruction area Y1, used as a first area, the bending stop area Y2, used as a second area, a centering area C, and a menu area Mn.

The endoscope image X imaged by the imaging portion 13 is arranged on the display screen Y. In an example in FIG. 2, a turbine blade is illustrated as an example of the endoscope image X.

The bending instruction area Y1 is disposed at a predetermined position on the display screen Y. In the example in FIG. 2, the bending instruction area Y1 is disposed in a lower right part of the endoscope image X. However, instead of in the lower right part, the bending instruction area Y1 may be disposed in any other part of the display screen Y.

As illustrated in FIG. 3, the bending instruction area Y1 is disposed like a ring. The bending instruction area Y1 includes a bending instruction pattern R1 that is visible to the user. The bending instruction pattern R1 is disposed between an outer edge Y1o and an inner edge Y1i of the bending instruction area Y1 and is disposed to be a ring concentric with the bending instruction area Y1. Direction instruction patterns R2 indicating bending directions are disposed on the bending instruction pattern R1. In an example in FIG. 3, the direction instruction patterns R2 include eight triangles arranged at equal intervals in a circumferential direction and respectively indicating an upward direction, a downward direction, a leftward direction, a rightward direction, and oblique directions. That is, the display screen Y includes the bending instruction area Y1 including the direction instruction patterns R2 indicating the bending directions. The bending instruction pattern R1 and the direction instruction patterns R2 are manipulation images used to manipulate the bending portion 14.

In the bending instruction area Y1, a bending instruction can be input by the user's first operation. In the bending instruction area Y1, the bending direction in the bending instruction is input according to a touch position in the circumferential direction.

The bending stop area Y2 is disposed inside of the bending instruction area Y1 disposed like a ring. In the bending stop area Y2, an instruction to stop bending of the bending portion 14 can be input according to the first operation. The control portion 25 stops a bending operation of the bending portion 14 when the first operation is performed on the bending stop area Y2. The bending stop area Y2 is disposed inside the bending instruction area Y1 but may be disposed both inside and outside the bending instruction area Y1.

In the centering area C, a centering instruction to straighten and place the bending portion 14 in a neutral position can be input by the user's second operation. In an example in FIGS. 2 to 5, the centering area C is the same as the bending stop area Y2. When the second operation lasting less than the predetermined duration from touch start until touch end is performed on the centering area C, the control portion 25 controllably causes the bending portion 14 to perform a centering operation of being straightened.

Operation buttons Bt are displayed in the menu area Mn. The operation buttons Bt allow instructions to execute predetermined functions to be input by the user's second operation. The predetermined functions include live image display, final recorded image display, thumbnail display, and the like. The operation buttons Bt may include a freeze button, a release button, a zoom button, a brightness adjustment button, or a menu button, which are used to execute predetermined functions. For example, when the user performs the second operation on the operation button Bt causing a live image display instruction to be input, the display screen Y switches to display of a live image. In other words, the menu area Mn is a second area with the operation buttons Bt allowing the predetermined functions to be executed.

For example, when the user performs the first operation by keeping in touch with an upper part of the bending instruction pattern R1 for the predetermined duration or more, the bending portion 14 is bent upward. When the user performs the first operation by sliding the finger F along the bending instruction pattern R1 from an upper part to a right part thereof as illustrated in an example in FIG. 4, the bending portion 14 changes from upward bending to rightward bending to rotate around a proximal end side of the bending portion 14. Even in a case where the finger F deviates from the bending instruction pattern R1, the user's bending instruction is input to the touch panel 22b so long as the finger F remains within the bending instruction area Y1. When the finger F slides from the bending instruction area Y1 into the bending stop area Y2 as a result of the first operation as illustrated in an example in FIG. 5, the bending portion 14 stops the bending operation. The user's first operation on the bending stop area Y2 does not cause the bending portion 14 to perform the bending operation.

That is, the display portion 22 includes the touch panel 22b to display the display screen Y including the endoscope image X acquired by the endoscope 21 including the bending portion 14. When the first operation lasting the predetermined duration or more from touch start until touch end on the display screen Y, the control portion 25 controllably causes the bending portion 14 to perform the bending operation. When the touch position in the first operation is in the bending instruction area Y1, the control portion 25 causes the bending portion 14 to perform the bending operation in a bending direction associated with the touch position.

A program for the bending control portion P causes a computer to execute a code for displaying, on the display portion 22 with the touch panel 22b, the display screen Y including the endoscope image X acquired by the endoscope 21 with the bending portion 14 and a code for controllably causing the bending portion 14 to perform the bending operation when the first operation lasting the predetermined duration or more from touch start until touch end is performed on the display screen Y.

A recording medium includes the program for the bending control portion P recorded therein, the program causing a computer to execute a code for displaying, on the display portion 22 with the touch panel 22b, the display screen Y including the endoscope image X acquired by the endoscope 21 with the bending portion 14 and a code for controllably causing the bending portion 14 to perform the bending operation when the first operation lasting the predetermined duration or more from touch start until touch end is performed on the display screen Y.

Operation of First Embodiment

Operation of the first embodiment will now be described.

Figure 6:
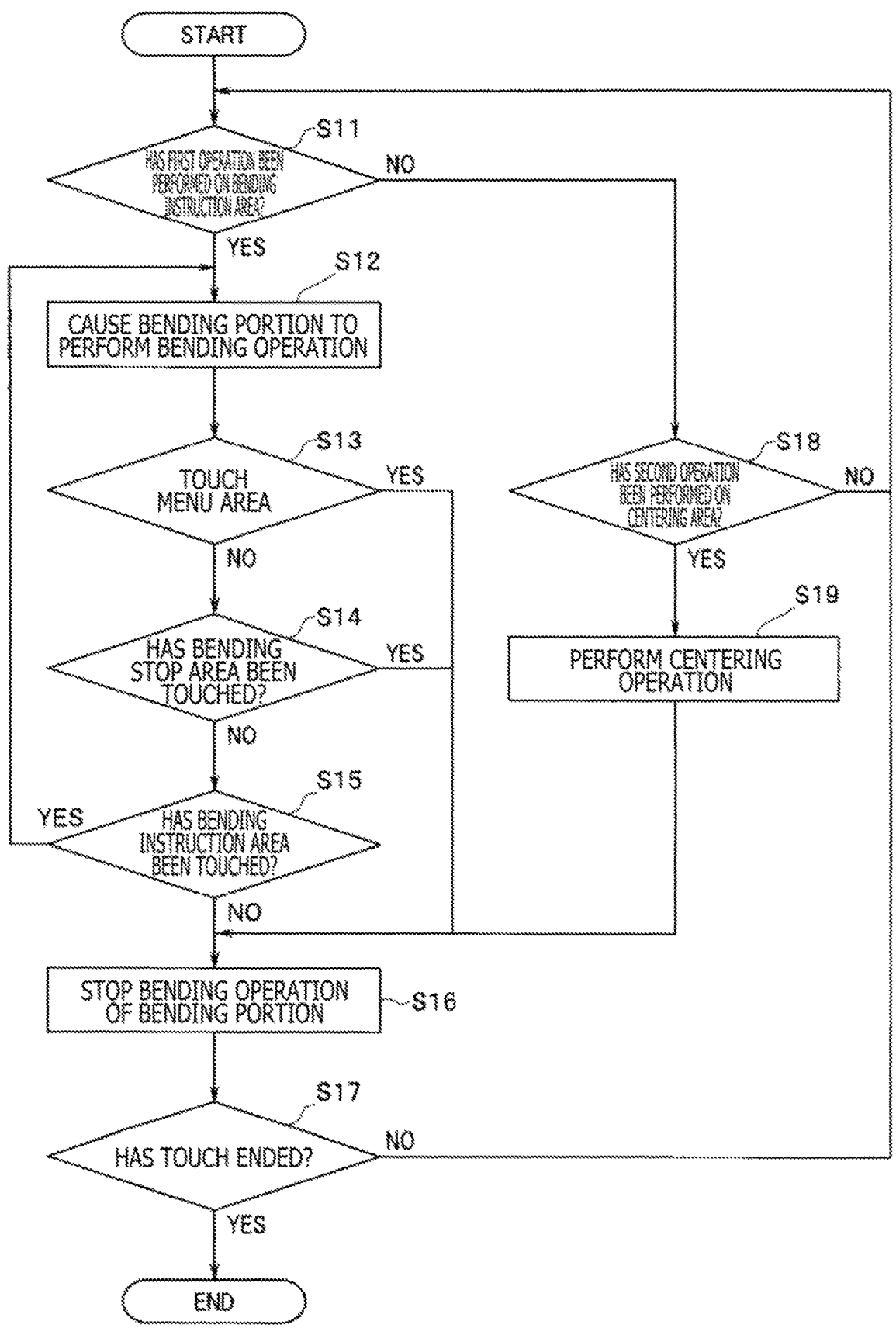
FIG. 6 is a flowchart illustrating an example of a bending control process of the touch panel device according to the first embodiment of the disclosed technology.
Figure 7:
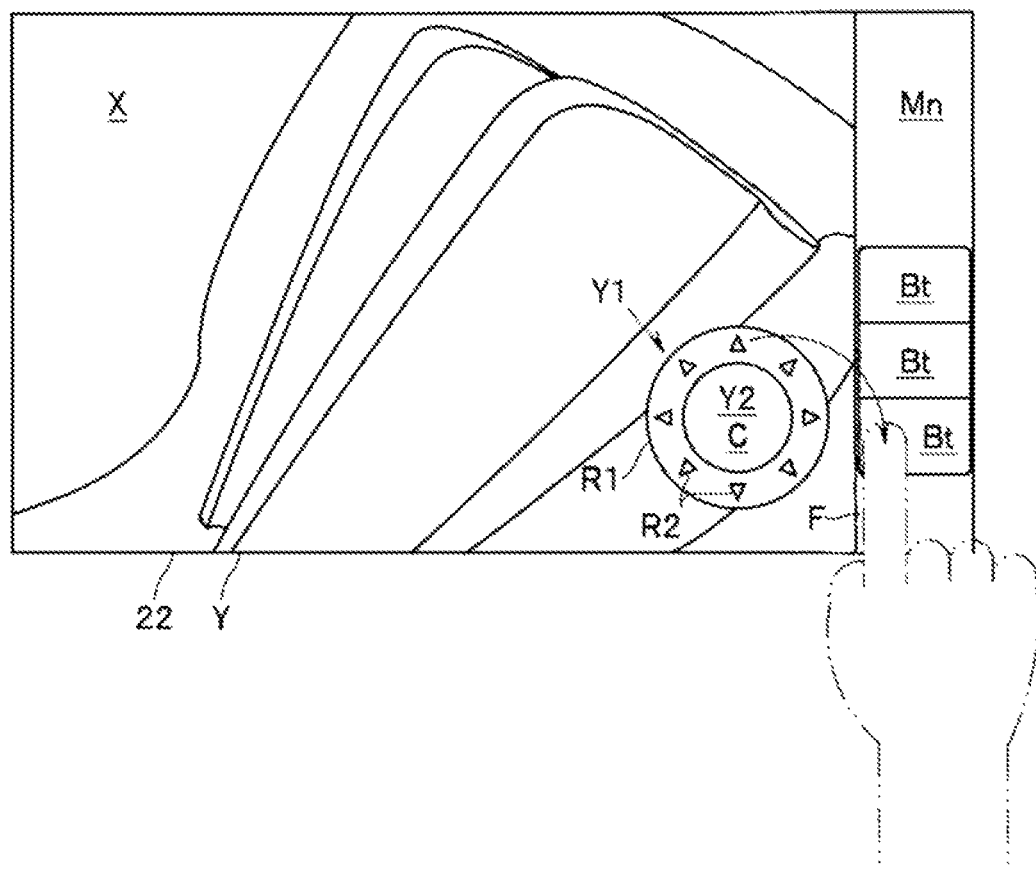
FIG. 7 is a diagram illustrating an example of a first operation of the touch panel device according to the first embodiment of the disclosed technology.
Figure 8:
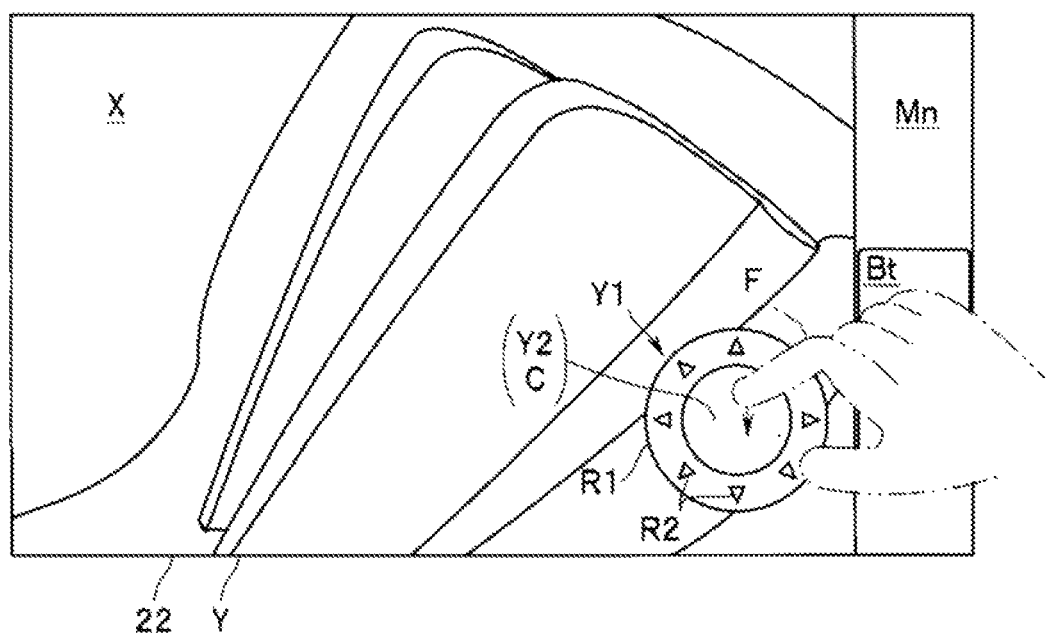
FIG. 8 is a diagram illustrating an example of a second operation of the touch panel device according to the first embodiment of the disclosed technology.

FIG. 6 is a flowchart illustrating an example of a bending control process of the touch panel device 31 according to the first embodiment of the disclosed technology. FIG. 7 is a diagram illustrating an example of the first operation of the touch panel device 31 according to the first embodiment of the disclosed technology. FIG. 8 is a diagram illustrating an example of the second operation of the touch panel device 31 according to the first embodiment of the disclosed technology.

The user activates the touch panel device 31 and inserts the insertion portion 11 of the endoscope 21 into the object. The imaging portion 13 images the inside of the object to output a resultant imaging signal to the image processing portion 15. The image processing portion 15 generates the endoscope image X based on the imaging signal to output the endoscope image X to the control portion 25. The control portion 25 generates the display screen Y based on the endoscope image X to output the display screen Y to the display portion 22. The display portion 22 displays the display screen Y. The control portion 25 loads the program for the bending control portion P from the storage portion 25b to execute the program.

Whether or not the first operation has been performed on the bending instruction area Y1 is determined in S11. The control portion 25 detects a touch in the bending instruction area Y1 based on a control signal input from the touch panel 22b. When detecting a touch, the control portion 25 drives an internal timer to measure the time until the touch is undetected. When the measured time is the predetermined duration or more, the control portion 25 determines that the first operation has been performed on the bending instruction area Y1. When it is determined in YES in S11 that the first operation has been performed on the bending instruction area Y1, the process proceeds to S12. On the other hand, when it is determined in NO in S11 that the first operation has not been performed on the bending instruction area Y1, the process proceeds to S18.

The bending operation of the bending portion 14 is performed the in S12. The control portion 25 detects the touch position on the bending instruction area Y1 based on the control signal input from the touch panel 22b. The control portion 25 executes a predetermined calculation to calculate the pulling amount of the pulling members based on the bending direction corresponding to the touch position. The control portion 25 outputs, to the bending driving portion 16, a bending instruction including the pulling amount of the pulling member. The bending driving portion 16 pulls the pulling members according to the bending instruction to bend the bending portion 14.

Whether or not the menu area Mn has been touched is determined in S13. The control portion 25 determines whether or not the touch position lies in the menu area Mn. When it is determined in NO in S13 that the menu area Mn has not been touched, the process proceeds to S14. On the other hand, when it is determined in YES in S13 that the menu area Mn has been touched, the process proceeds to S16.

Whether or not the bending stop area Y2 has been touched is determined in S14. The control portion 25 determines whether or not the bending stop area Y2 has been touched. When it is determined in NO in S14 that the bending stop area Y2 has not been touched, the process proceeds to S15. On the other hand, when it is determined in YES in S14 that the bending stop area Y2 has been touched, the process proceeds to S16.

Whether or not the bending instruction area Y1 has been touched is determined in S15. The control portion 25 determines whether or not the bending instruction area Y1 has been touched. When it is determined in YES in S15 to that the bending instruction area Y1 has been touched, the process returns to S12. On the other hand, when it is determined in NO in S15 the bending instruction area Y1 has not been touched, the process proceeds to S16.

The bending operation of the bending portion 14 is stopped in S16. The control portion 25 outputs the control signal to the bending driving portion 16 to stop the bending operation.

Whether or not the touch has ended is determined in S17. The control portion 25 determines whether or not the touch has ended based on the control signal input from the touch panel 22b. When the touch on the touch panel 22b is undetected, the control portion 25 determines that the touch has ended. When the touch has not ended in NO in S17, the process returns to S11. On the other hand, when the touch has ended in YES in S17, the bending control process ends.

Whether or not the second operation has been performed on the centering area C is determined in S18. The control portion 25 determines, based on the time measured by the timer and the control signal input from the touch panel 22b, whether or not a touch lasting less than the predetermined duration has been performed in the endoscope image X. When a touch lasting less than the predetermined duration has been performed in the endoscope image X, the control portion 25 determines in YES in S18 that the second operation has been performed. The process proceeds to S19. On the other hand, when the control portion 25 determines in NO in S18 that the second operation has not been performed, the process returns to S11.

The centering operation is performed in S19. The control portion 25 outputs a centering instruction to the bending driving portion 16. When the centering instruction is input to the bending driving portion 16, the bending driving portion 16 pulls the pulling members to straighten the bending portion 14. After the centering operation is carried out, the process proceeds to S16.

The process in S11 to S19 is included in the process of the bending control portion P.

In other words, an endoscope bending control method involves preparing the display portion 22 with the touch panel 22b displaying the display screen Y, displaying, on the display portion 22, the display screen Y including the endoscope image X acquired by the endoscope 21 with the bending portion 14, and controllably causing the bending portion 14 to perform the bending operation when the first operation lasting the predetermined duration or more from touch start until touch end is performed on the display screen Y.

For example, when the user performs the first operation on the bending instruction area Y1 in S11, the bending portion 14 is bent in S12. As an imaged part on the object varies, the endoscope image X also varies so as to scroll on the display screen Y. When, in NO in S13 and YES in S14, the finger F slides into the bending instruction area Y2 as a result of the first operation, the bending portion 14 stops the bending operation in S16. When, in NO in S17 and YES in S11, the finger F slides into the bending instruction area Y1 again as a result of the first operation, the bending portion 14 performs the bending operation in S12.

With the user's eyes fixed at the endoscope image X, the user places the finger F at the approximate position of the bending instruction area Y1. The user subsequently performs the first operation by sliding the finger F in any direction. The user stores the position of the finger F placed when scrolling of the endoscope image X is started or stopped. This allows the user to determine a contour of the bending instruction area Y1 based on the stored position of the finger F and in turn to determine, based on the determined contour, a touch position in the bending instruction area Y1 to be touched to specify the bending direction.

Furthermore, when the finger F slides into the menu area Mn as a result of the first operation in YES in S14 as illustrated in FIG. 7, the bending portion 14 stops the bending operation in S16. The user can determine the position of the menu area Mn with no need to shift the user's eyes to the menu area Mn and with the user's eyes fixed at the endoscope image X. This can prevent possible erroneous operation of the operation buttons Bt.

When, in NO in S11 and YES in S18, the second operation is determined to have been performed on the centering area C, the bending portion 14 performs the centering operation in S19. The user can more reliably input the centering instruction with the user's eyes fixed at the endoscope image X.

According to the embodiment, the touch panel device 31 allows the bending portion 14 of the insertion portion 11 to be more accurately manipulated by the bending instruction and the centering instruction with no need to shift the user's eyes to the bending instruction pattern R1 or the direction instruction patterns R2 and with the user's eyes fixed at the endoscope image X.

Modified Example of First Embodiment

In the first embodiment, the bending instruction area Y1 is disposed like a ring concentric with the bending instruction pattern R1. However, the bending instruction area Y1 need not necessarily be disposed like a ring concentric with the bending instruction pattern R1.

Figure 9:
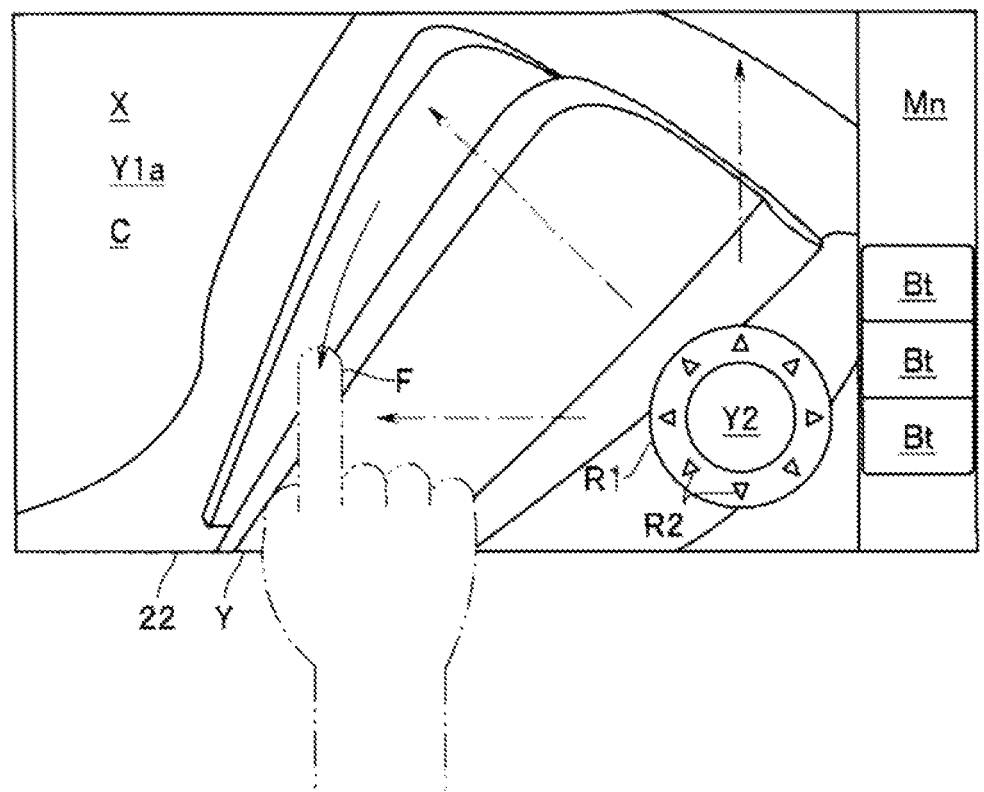
FIG. 9 is a diagram illustrating an example of the first operation of the touch panel device according to a modified example of the first embodiment of the disclosed technology.
Figure 10:
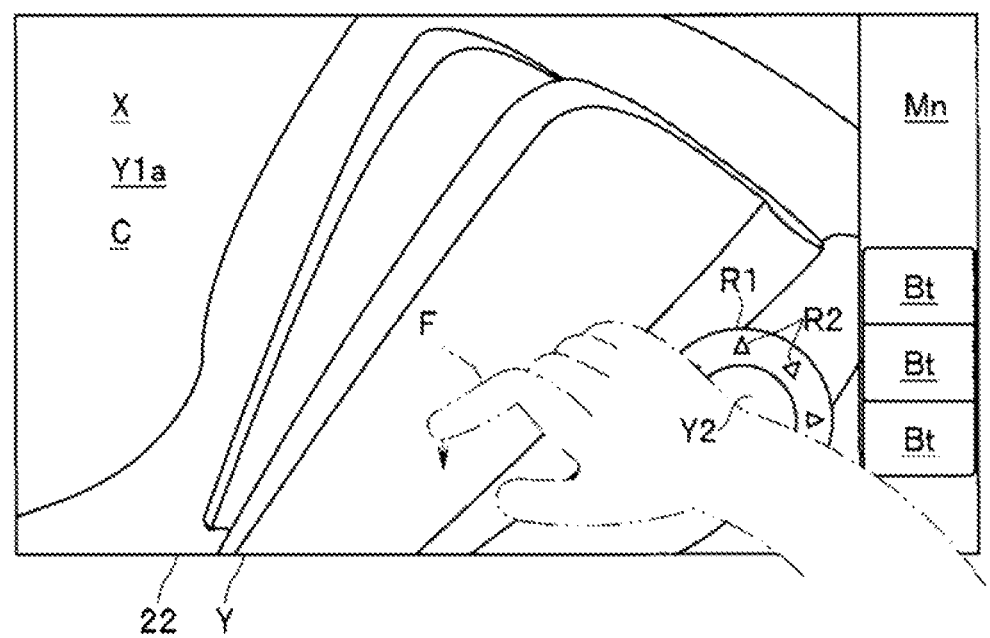
FIG. 10 is a diagram illustrating an example of the second operation of the touch panel device according to the modified example of the first embodiment of the disclosed technology.

FIG. 9 is a diagram illustrating an example of the first operation of the touch panel device 31 according to a modified example of the first embodiment of the disclosed technology. FIG. 10 is a diagram illustrating an example of the second operation of the touch panel device 31 according to the modified example of the first embodiment of the disclosed technology. In the modified example, details of the same components as those of other embodiments and modified examples are omitted. In the other embodiments and modified examples, details of the same components are also omitted.

As illustrated in FIG. 9, the bending instruction area Y1a is arranged outside the bending instruction pattern R1. In the bending instruction area Y1a, touch positions indicating bending directions are arranged in radial directions around the bending instruction pattern R1 (alternate one and short dash lines in FIG. 9). The bending stop area Y2 is arranged inside the bending instruction pattern R1. The centering area C is arranged all over the endoscope image X.

For example, when the user performs the first operation by sliding the finger F obliquely downward and leftward in a central part of the bending instruction area Y1a, the bending portion 14 is bent obliquely downward and leftward in response to movement of the finger F. When the user performs the first operation on the bending stop area Y2, the bending portion 14 stops the bending operation.

When the user performs the second operation on the centering area C as illustrated in FIG. 10, the bending portion 14 performs the centering operation.

Thus, with the user's eyes fixed at the endoscope image X, the user can input the instruction to bend the bending portion 14 by performing the first operation on the bending instruction area Y1a and also input the instruction to center the bending portion 14 by performing the second operation on the centering area C.

Second Embodiment

In the first embodiment and the modified example, the display screen Y includes the menu area Mn. However, the display screen Y need not necessarily include the menu area Mn.

Figure 11:
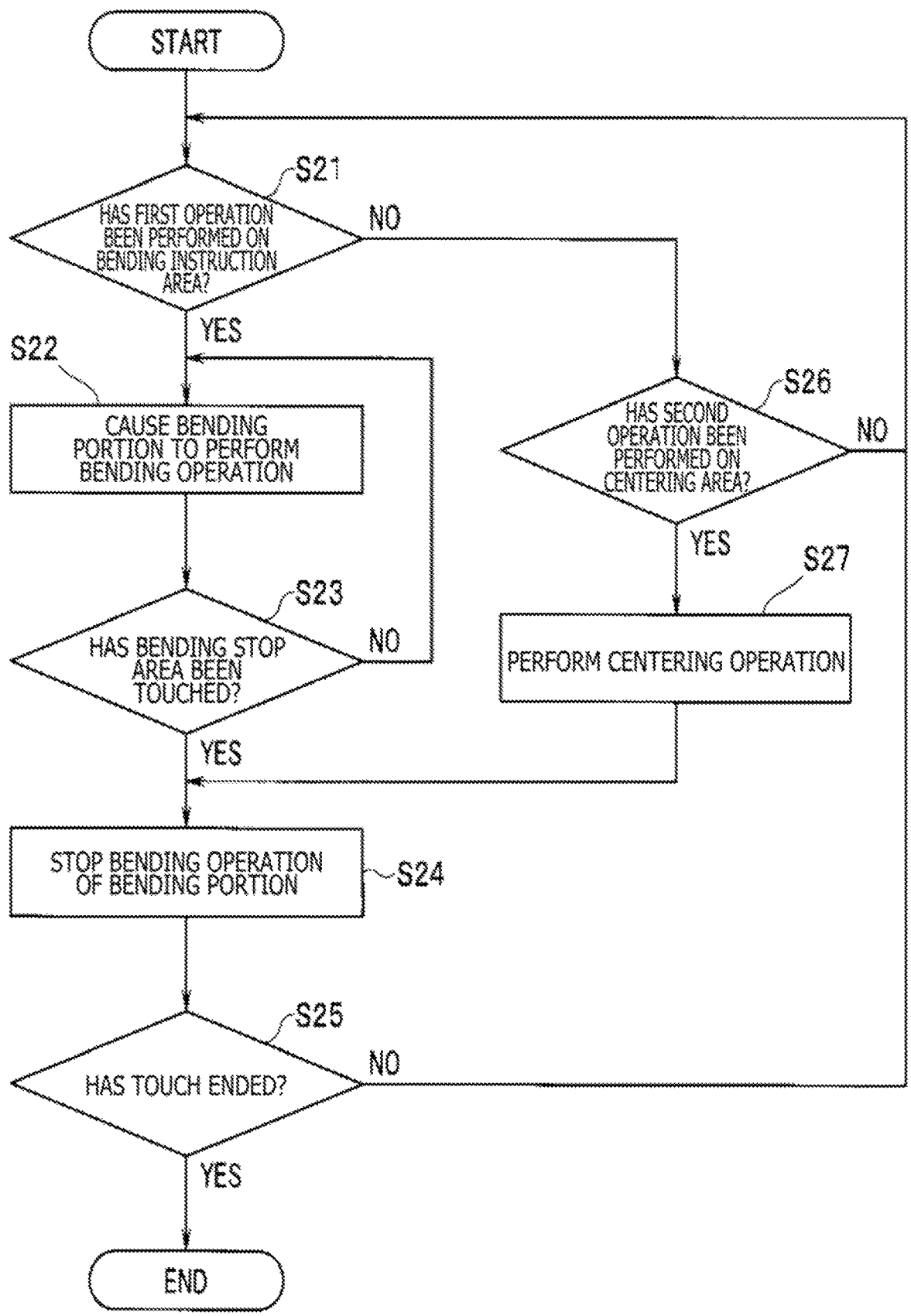
FIG. 11 is a flowchart illustrating an example of the bending control process of the touch panel device according to a second embodiment of the disclosed technology.
Figure 12:
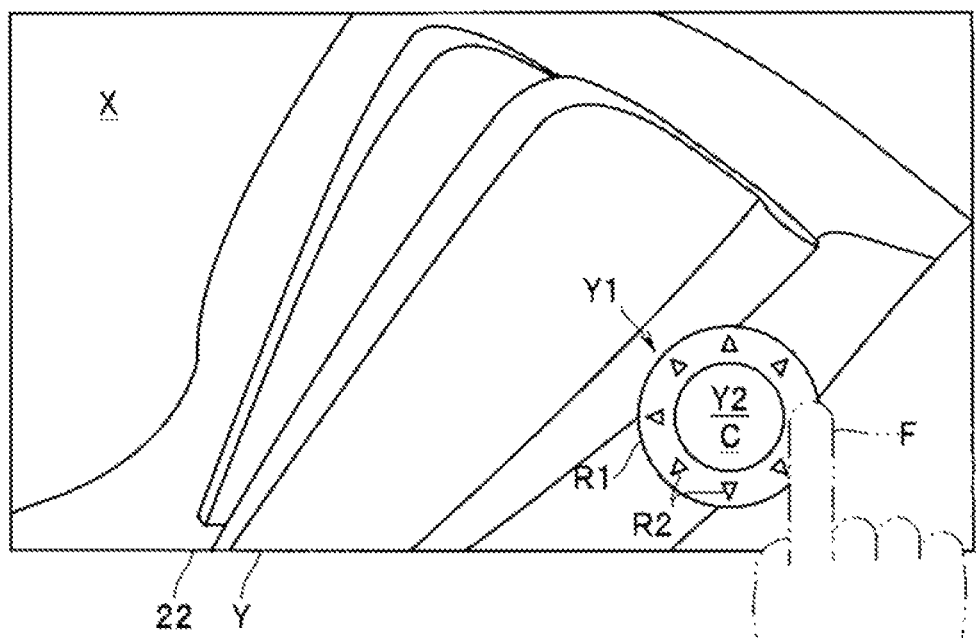
FIG. 12 is a diagram illustrating an example of the first operation of the touch panel device according to the second embodiment of the disclosed technology.
Figure 13:
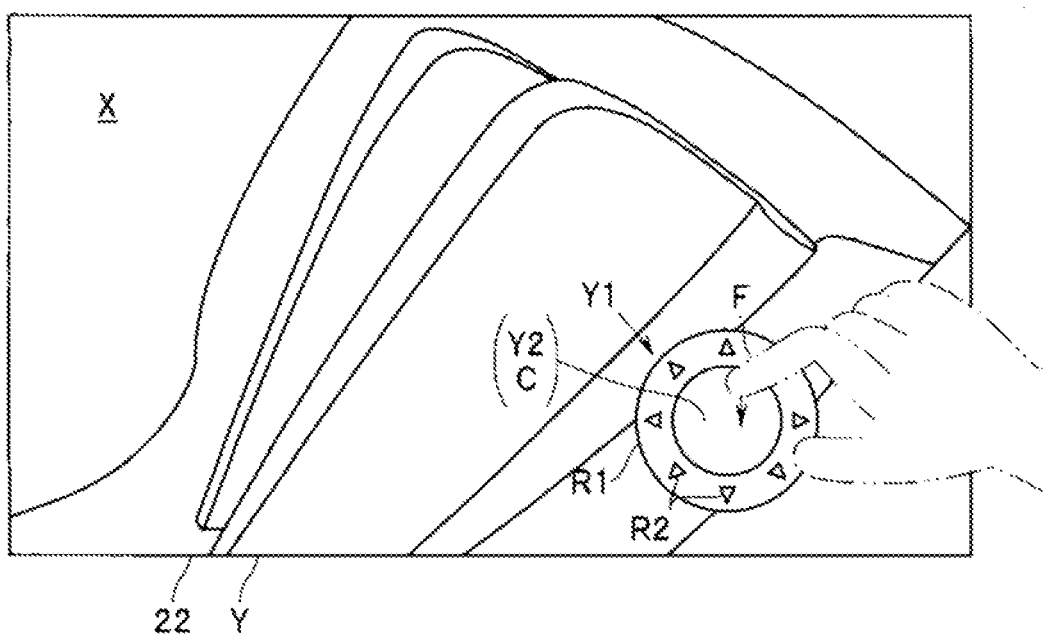
FIG. 13 is a diagram illustrating an example of the second operation of the touch panel device according to the second embodiment of the disclosed technology.

FIG. 11 is a flowchart illustrating an example of the bending control process of the touch panel device 31 according to a second embodiment of the disclosed technology. FIG. 12 is a diagram illustrating an example of the first operation of the touch panel device 31 according to the second embodiment of the disclosed technology. FIG. 13 is a diagram illustrating an example of the second operation of the touch panel device 31 according to the second embodiment of the disclosed technology.

In the second embodiment, the endoscope image X is displayed all over the display screen Y. The bending instruction area Y1 is arranged in a lower right part of the endoscope image X. The bending stop area Y2 is arranged inside the bending instruction area Y1. The centering area C is the same as the bending stop area Y2.

Operation of the second embodiment will be described.

Whether or not the first operation has been performed on the bending instruction area Y1 is determined in S21. When the first operation is determined in YES in S21 to have been performed on the bending instruction area Y1, the process proceeds to S22. On the other hand, when the first operation is determined in NO in S21 not to have been performed on the bending instruction area Y1, the process proceeds to S26.

The bending portion 14 is caused to perform the bending operation in S22.

Whether or not the bending stop area Y2 has been touched is determined in NO in S23. When the bending stop area Y2 is determined in S23 not to have been touched, the process returns to S22. On the other hand, when the bending stop area Y2 is determined in YES in S23 to have been touched, the process proceeds to S24.

The bending operation of the bending portion 14 is stopped in S24.

Whether or not the touch has ended is determined in S25. When the touch is determined in NO in S25 not to have ended, the process returns to S21. On the other hand, when the touch is determined in YES in S25 to have ended, the process ends.

Whether or not the second operation has been performed on the centering area C is determined in S26. When the second operation is determined in YES in S26 to have been performed on the centering area C, the process proceeds to S27. On the other hand, when the second operation is determined in NO in S26 not to have been performed on the centering area C, the process returns to S21.

The centering operation is performed in S27. After the centering operation is carried out, the process proceeds to S24.

The process in S21 to S27 is included in the process of the bending control portion P.

For example, when the user performs the first operation on the bending instruction area Y1 as illustrated in FIG. 12, the bending portion 14 performs the bending operation in response to movement of the finger F.

When the user performs the second operation as illustrated in FIG. 13, the bending portion 14 performs the centering operation.

According to the embodiments, the touch panel device 31 can display the endoscope image X wider. This allows the bending portion 14 of the insertion portion 11 to be more accurately manipulated by the bending instruction and the centering instruction with no need to shift the user's eyes to the bending instruction pattern R1 or the direction instruction patterns R2 and with the user's eyes fixed at the endoscope image X.

Modified Example of Second Embodiment

In the second embodiment, the direction instruction patterns R2 are disposed in the bending instruction pattern R1 located in the lower right part of the endoscope image X. However, direction instruction patterns R2a may be disposed at peripheral edges of the endoscope image X.

Figure 14:
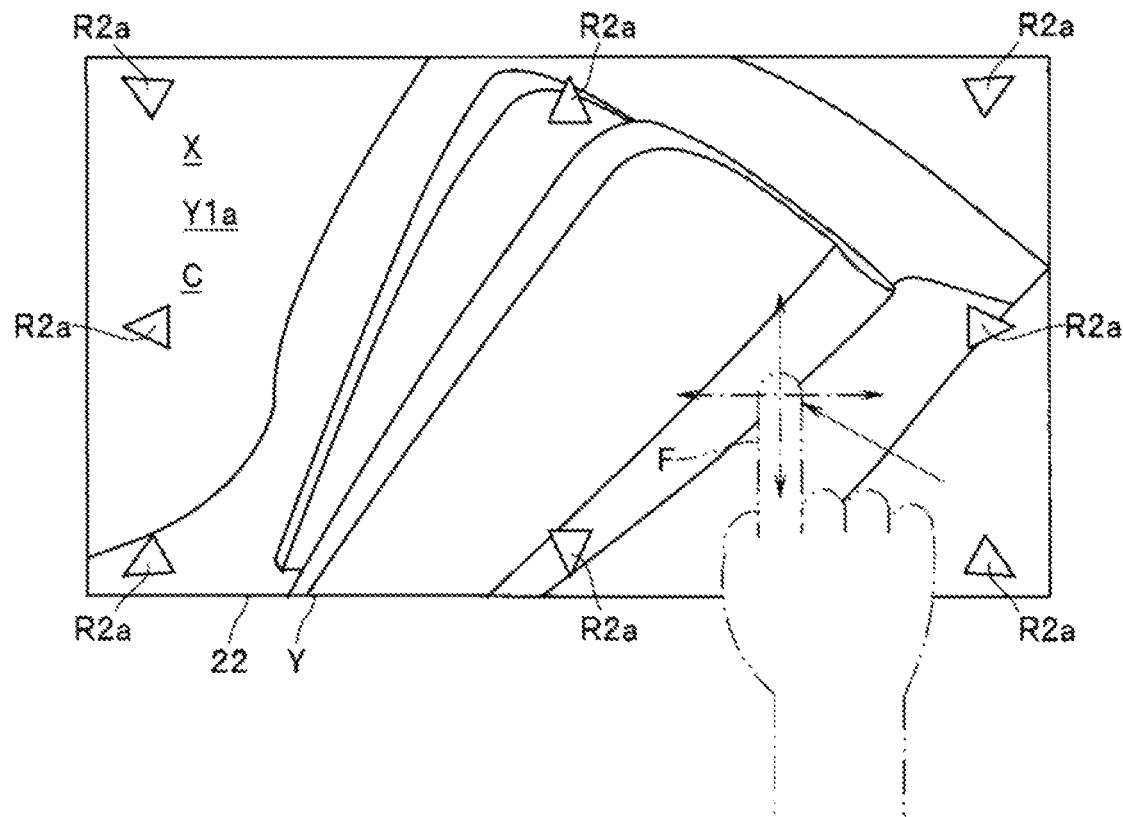
FIG. 14 is a diagram illustrating an example of the first operation of the touch panel device according to a modified example of the second embodiment of the disclosed technology.
Figure 15:
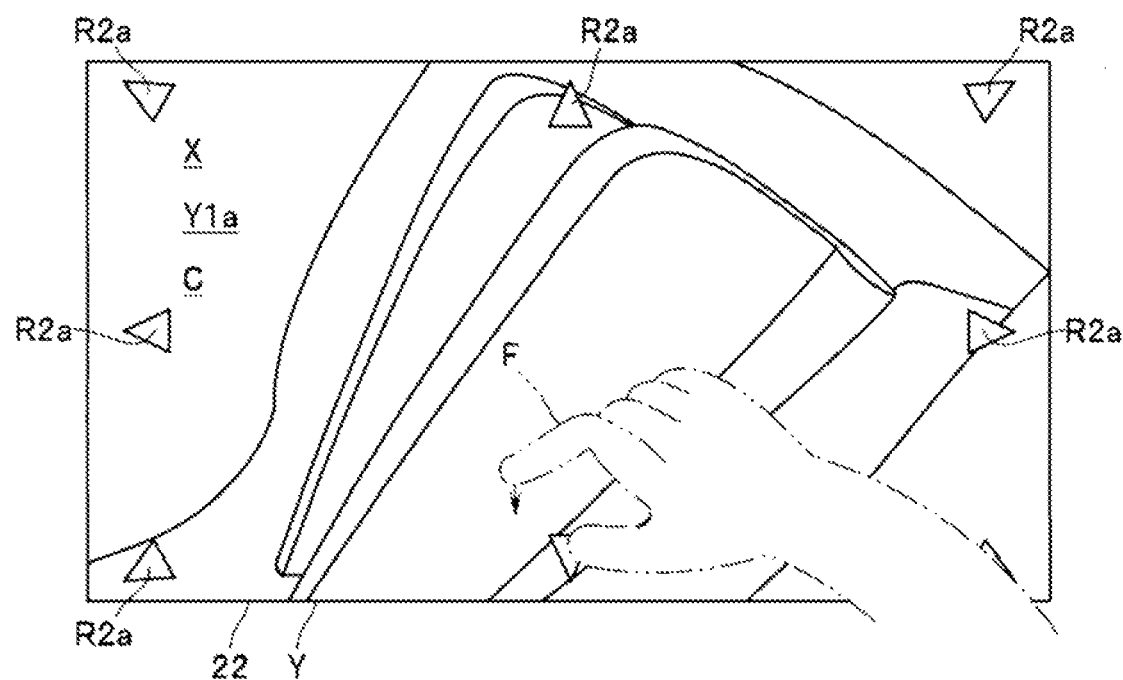
FIG. 15 is a diagram illustrating an example of the second operation of the touch panel device according to the modified example of the second embodiment of the disclosed technology.

FIG. 14 is a diagram of the first operation of the touch panel device 31 according to a modified example of the second embodiment of the disclosed technology. FIG. 15 is a diagram of the second operation of the touch panel device 31 according to the modified example of the second embodiment of the disclosed technology.

As illustrated in FIG. 14, the bending instruction area Y1a and the centering area C are arranged all over the endoscope image X. The peripheral edges of a display area of the endoscope image X include eight direction instruction patterns R2a indicating eight directions including an upward direction, a downward direction, a leftward direction, a rightward direction, and oblique direction.

As illustrated by alternate long and short dash lines in FIG. 14, the bending direction of the bending portion 14 is a direction corresponding to the first operation. For example, when the user performs the first operation on the bending instruction area Y1a by sliding the finger F upward and leftward, the bending portion 14 performs an upward and leftward bending operation in response to the movement of the finger F.

When the user performs the second operation on the centering area C as illustrated in FIG. 15, the bending portion 14 performs the centering operation.

Third Embodiment

The first embodiment, the second embodiment, and the modified examples of the first and second embodiments, the bending instruction pattern R1 and the direction instruction patterns R2 and R2a are disposed on the display screen Y. However, the bending instruction pattern R1 and the direction instruction patterns R2 and R2a need not necessarily be disposed.

Figure 16:
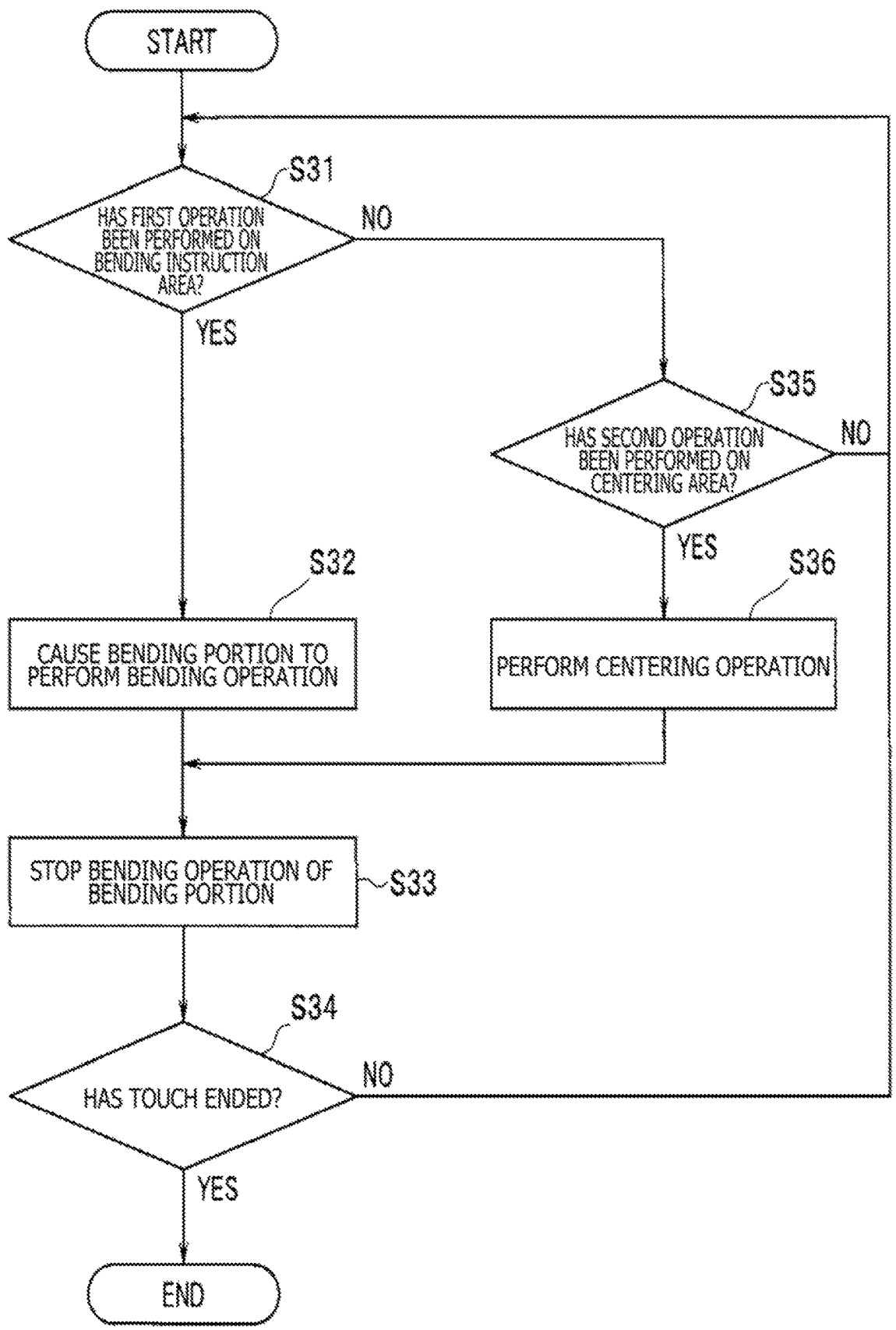
FIG. 16 is a flowchart illustrating an example of the bending control process of the touch panel device according to a third embodiment of the disclosed technology.

FIG. 16 is a flowchart illustrating an example of the bending control process of the touch panel device 31 according to a third embodiment of the disclosed technology. FIG.

Figure 18:
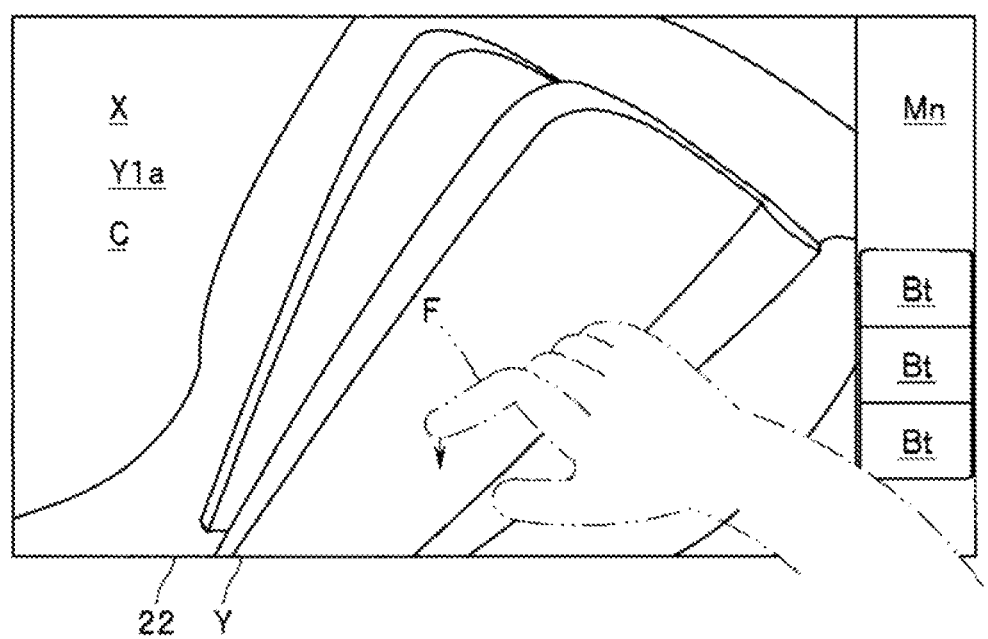
FIG. 18 is a diagram illustrating an example of the second operation of the touch panel device according to the third embodiment of the disclosed technology.

17 is a diagram illustrating an example of the first operation of the touch panel device 31 according to the third embodiment of the disclosed technology. FIG. 18 is a diagram illustrating an example of the second operation of the touch panel device 31 according to the third embodiment of the disclosed technology.

In the third embodiment, the endoscope image X and the menu area Mn are disposed on the display screen Y.

Figure 17:
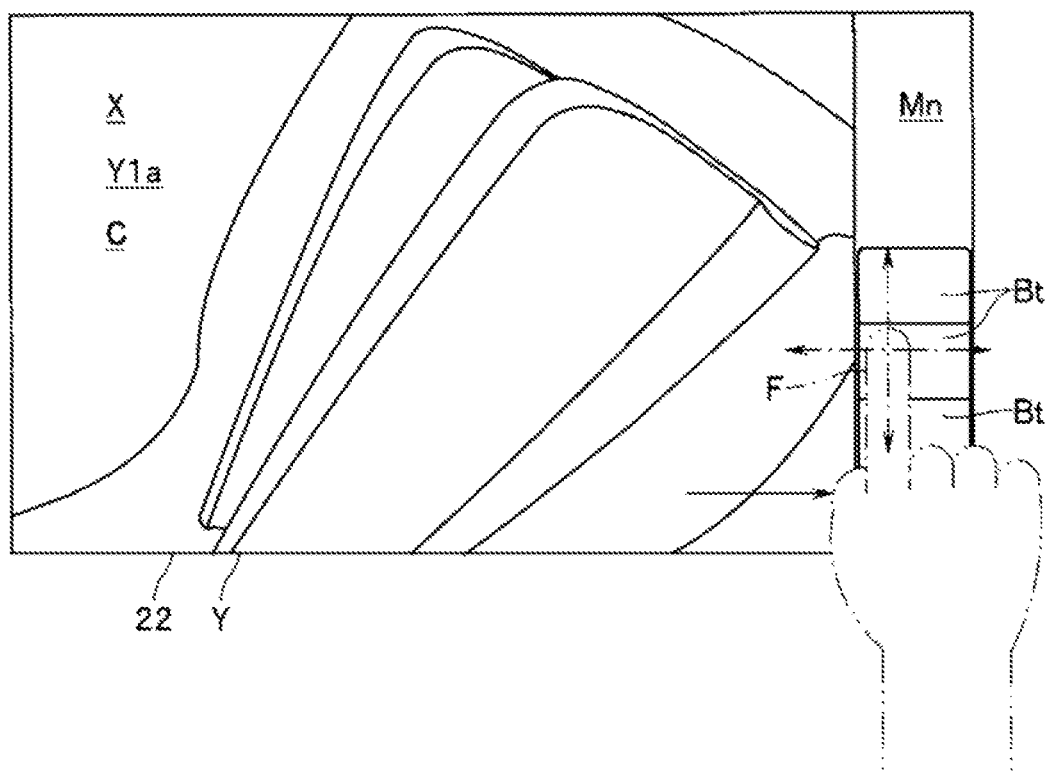
FIG. 17 is a diagram illustrating an example of the first operation of the touch panel device according to the third embodiment of the disclosed technology.

As illustrated in FIG. 17, the bending instruction area Y1a and the centering area C are arranged all over the endoscope image X. When the user performs the first operation on the bending instruction area Y1a, the bending portion 14 performs the bending operation in the direction corresponding to the first operation.

When the user performs the second operation on the centering area C as illustrated in FIG. 18, the bending portion 14 performs the centering operation.

Operation of the third embodiment will be described.

Whether or not the first operation has been performed on the bending instruction area Y1 is determined in YES in S31. When the first operation is determined in S31 to have been performed on the bending instruction area Y1, the process proceeds to S32. On the other hand, when the first operation is determined in NO in S31 not to have been performed on the bending instruction area Y1, the process proceeds to S35.

The bending portion 14 is caused to perform the bending operation in S32.

The bending operation of the bending portion 14 is stopped in S33.

Whether or not the touch has ended is determined in S34. When the touch is determined in NO in S34 not to have ended, the process returns to S31. On the other hand, when the touch is determined in YES in S34 to have ended, the bending control process ends.

Whether or not the second operation has been performed on the centering area C is determined in S35. When the second operation is determined in YES in S35 to have been performed, the process proceeds to S36. On the other hand, when the second operation is determined in NO in S35 not to have been performed, the process returns to S31.

The centering operation is performed in S36. After the centering operation is carried out, the process proceeds to S33.

The process in S31 to S36 is included in the process of the bending control portion P.

For example, when the user performs the first operation on the bending instruction area Y1 as illustrated in FIG. 17, the bending portion 14 is bent in response to the movement of the finger F.

When the user performs the second operation on the centering area C as illustrated in FIG. 18, the bending portion 14 performs the centering operation.

According to the embodiments, the touch panel device 31 can display the endoscope image X wider. This allows the bending portion 14 of the insertion portion 11 to be more accurately manipulated by the bending instruction and the centering instruction with the user's eyes fixed at the endoscope image X.

Modified Example of Third Embodiment

In the third embodiment, the menu area Mn is disposed on the display screen Y. However, the menu area Mn need not necessarily be disposed.

Figure 19:
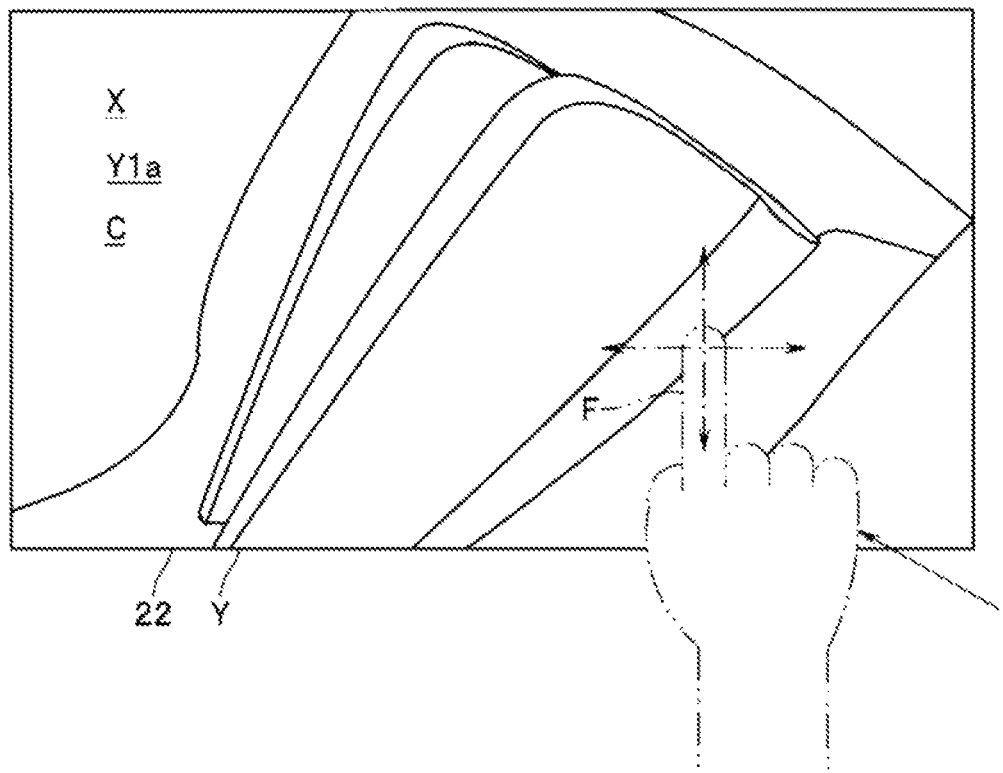
FIG. 19 is a diagram illustrating an example of the first operation of the touch panel device according to a modified example of the third embodiment of the disclosed technology.
Figure 20:
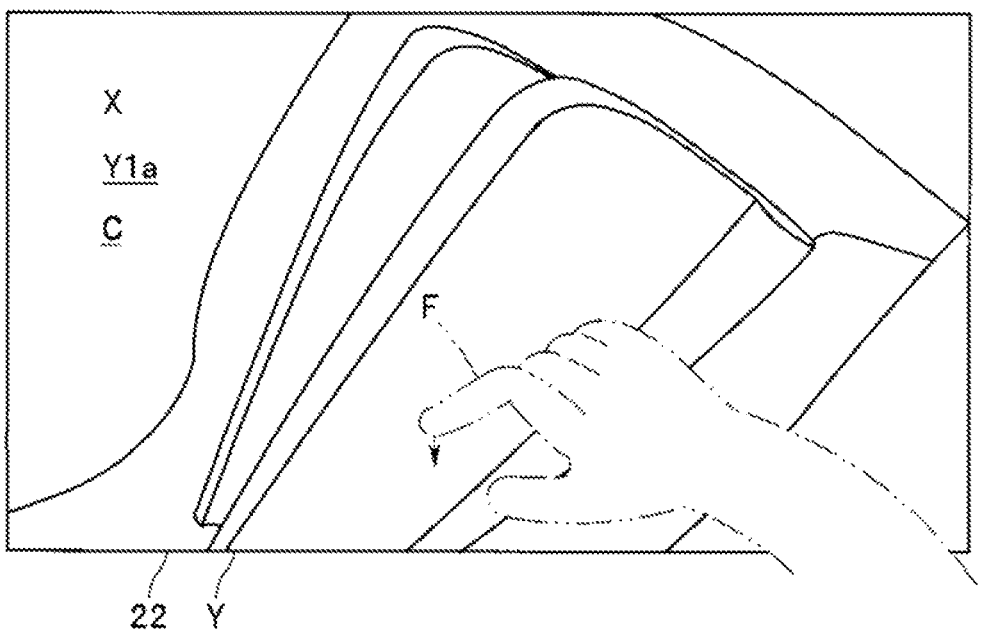
FIG. 20 is a diagram illustrating an example of the second operation of the touch panel device according to the modified example of the third embodiment of the disclosed technology.

FIG. 19 is a diagram illustrating an example of the first operation of the touch panel device 31 according to a modified example of the third embodiment of the disclosed technology. FIG. 20 is a diagram illustrating an example of the second operation of the touch panel device 31 according to the modified example of the third embodiment of the disclosed technology.

As illustrated in FIG. 19, the bending instruction area Y1a and the centering area C are arranged all over the endoscope image X. When the user performs the first operation on the bending instruction area Y1a, the bending portion 14 performs the bending operation in the direction corresponding to the first operation.

When the user performs the second operation on the centering area C as illustrated in FIG. 20, the bending portion 14 performs the centering operation.

In the first embodiment and the second embodiment, the bending instruction pattern R1 illustrated between the outer edge Y1o and the inner edge Y1i of the bending instruction area Y1 is disposed like a ring concentric with the outer edge Y1o and the inner edge Y1i. However, the bending instruction pattern R1 may be disposed to occupy the same area as the bending instruction area Y1.

In the first embodiment, when the first operation is performed on the menu area Mn, the bending portion 14 stops the bending operation. However, with the operation of the bending portion 14 not stopped, the menu area Mn may be moved to a position different from the touch position.

In the embodiments and the modified examples, the bending portion 14 performs the bending operation according to the first operation. However, the bending operation may be stopped in response to stoppage of movement of the finger F or may continue even after movement of the finger F is stopped.

In the embodiments and the modified examples, a bending speed may vary according to a swipe speed.

In the embodiments and the modified examples, the bending speed may be reduced by performing the first operation in a direction opposite to the bending direction.

In the embodiments and the modified examples, the endoscope image X may include areas for providing instructions regarding the bending speed, such as an instruction area for high-speed bending, an instruction area for medium-speed bending, and an instruction area for low-speed bending, the instruction areas allowing the respective instructions to be input by the first operation.

In the embodiments and the modified examples, the second operation is used to input the centering instruction, and the first operation is used to input the bending instruction. However, the second operation may allow input of an angle lock instruction to lock the bending portion 14 in a bent state by the second operation. The first operation may allow the bending instruction to be input.

For the steps of the procedures in the present embodiments, the order of execution may be changed, a plurality of the steps may be simultaneously executed, or the order of execution may be varied for each case of execution, unless these modifications are contrary to the nature of the steps. Moreover, all or some of the steps of the procedures in the present embodiments may be implemented by hardware.

In sum, one aspect of the disclosed technology is directed to a touch panel device used in an endoscope device. The touch panel device includes a display portion having a display panel and a touch panel formed thereto and configured to display an endoscope image on the display panel acquired by an endoscope including a bending portion. A processor is configured to control the bending portion so as to perform a bending operation when a user keeps performing a first operation on the touch panel in a first predetermined duration or more.

The processor is configured to control the bending portion so as to perform a bending operation so that the bending portion is accurately manipulated with no need for a user to shift eyes from the endoscope image to a manipulation image during an operation. The display panel displays a first area with direction instruction patterns indicating bending directions. The processor directs the bending operation to be performed in the bending direction associated with a touch position in the first operation when the touch position is corresponding to the first area. The display panel displays a second area inside the first area. The processor is configured to stop the bending operation when the first operation is performed on the second area via the touch panel. The display panel displays a centering area. The processor is configured to control the bending portion so that the bending portion is straightened when the user keeps performing a second operation on the centering area via the touch panel in a second predetermined duration less than the first predetermined duration of the first operation. The second area on the display panel is substantially same as the centering area on the display panels. The centering area on the display panel is an area outside the first area on the display panel. The second area on the display panel is disposed inside the first area arranged like a ring on the display panel. The display panel displays a second area outside the first area. The processor stops the bending operation when the first operation is performed on the second area via the touch panel.

The display panel displays a centering area and the processor is configured to control the bending portion so that the bending portion is straightened when the user keeps performing a second operation on the centering area via the touch panel in a duration less than a second predetermined duration. The second area is substantially same as the centering area on the display panel. The second area is disposed inside the first area arranged like a ring on the display panel. The display panel displays a second area in which the processor is configured to stop the bending operation when the user performs the first operation on the second area via the touch panel. The display panel displays an operation button for executing a predetermined function in the second area. The display panel displays a second area in which the processor is configured to stop the bending operation when the user performs the first operation on the second area via the touch panel. The display panel displays a centering area and the processor is configured to control the bending portion so that the bending portion is straightened when the user keeps performing a second operation on the centering area via the touch panel in a duration less than the first predetermined duration. The second area is substantially same as the centering area on the display panel. The display panel displays a centering area and the processor is configured to control the bending portion so that the bending portion is straightened when the user keeps performing a second operation on the centering area via the touch panel in a second predetermined duration less than the first predetermined duration of the first operation.

Another aspect of the disclosed technology is directed to a recording medium used in a touch panel device including a bending control program recorded therein. The bending control program is causing a computer to execute: a code displaying on a display portion with a touch panel, a display screen including an endoscope image acquired by an endoscope having a bending portion and a code controls the bending portion so as to perform a bending operation when a user keeps performing a first operation on the touch panel in a first predetermined duration or more.

A further aspect of the disclosed technology is directed to an endoscope bending control method comprising the steps preparing a display portion having a touch panel displaying a display screen; displaying, on the display portion, the display screen including an endoscope image acquired by an endoscope having a bending portion; and controlling the bending portion so as to perform a bending operation when a user keeps performing a first operation on the touch panel in a first predetermined duration or more.

The disclosed technology is not limited to the embodiments described hereinbefore. Various changes, alterations, and the like can be made to the embodiments without departing from the spirits of the disclosed technology.

It should be understood by those skilled in the art that various modifications, combinations, sub-combinations and alterations may occur depending on design requirements and other factors insofar as they are within the scope of the appended claims or the equivalents thereof.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A touch panel device used in an endoscope device comprising:
    a display portion having a display panel and a touch panel formed thereto and configured to display an endoscope image on the display panel acquired by an endoscope including a bending portion; and
    a processor configured to control the bending portion so as to perform a bending operation when a user keeps performing a first operation on the touch panel in a first predetermined duration or more and wherein the display panel displays respective concentric first and second areas in which the second area being disposed inside the first area forming a ring configuration with direction instruction patterns indicating bending direction therebetween and the processor directs the bending operation to be performed in the bending direction associated with a touch position in the first operation when the touch position is corresponding to the first area and wherein the processor being configured to stop the bending operation when the user swipes on the direction instruction patterns in the second area;
    wherein the processor changes a speed of the bending operation of the bending portion according to an operation speed of the first operation.

2. The touch panel device of claim 1, wherein the processor is configured to control the bending portion so as to perform a bending operation so that the bending portion is accurately manipulated with no need for a user to shift eyes from the endoscope image to a manipulation image during an operation.

3. The touch panel device of claim 1, wherein the display panel displays a centering area, and the processor is configured to control the bending portion so that the bending portion is straightened when the user keeps performing a second operation on the centering area via the touch panel in a second predetermined duration less than the first predetermined duration of the first operation.

4. The touch panel device of claim 3, wherein the second area on the display panel is substantially same as the centering area on the display panels.

5. The touch panel device of claim 3, wherein the centering area on the display panel is an area outside the first area on the display panel.

6. The touch panel device of claim 1, wherein the display panel displays a second area outside the first area, and the processor stops the bending operation when the first operation is performed on the second area via the touch panel.

7. The touch panel device of claim 6, wherein the display panel displays a centering area, and the processor is configured to control the bending portion so that the bending portion is straightened when the user keeps performing a second operation on the centering area via the touch panel in a duration less than a second predetermined duration.

8. The touch panel device of claim 7, wherein the second area is substantially same as the centering area on the display panel.

9. The touch panel device of claim 1, wherein the display panel displays a second area wherein the processor is configured to stop the bending operation when the user performs the first operation on the second area via the touch panel, and the display panel displays an operation button for executing a predetermined function in the second area.

10. The touch panel device of claim 1, wherein the display panel displays a second area wherein the processor is configured to stop the bending operation when the user performs the first operation on the second area via the touch panel.

11. The touch panel device of claim 10, wherein the display panel displays a centering area, and the processor is configured to control the bending portion so that the bending portion is straightened when the user keeps performing a second operation on the centering area via the touch panel in a duration less than the first predetermined duration.

12. The touch panel device of claim 11, wherein the second area is substantially same as the centering area on the display panel.

13. The touch panel device of claim 1, wherein the display panel displays a centering area, and the processor is configured to control the bending portion so that the bending portion is straightened when the user keeps performing a second operation on the centering area via the touch panel in a second predetermined duration less than the first predetermined duration of the first operation.

14. A computer program product in a form of recording medium, used in a touch panel device, including a non-transitory computer readable medium having a bending control program code encoded thereon that when executed by a processor of a computer, the bending control program causes the computer to execute:
    a code displaying, on a display portion having a display screen and a touch panel formed thereto, the display screen includes an endoscope image acquired by an endoscope having a bending portion;
    a code controls the bending portion so as to perform a bending operation when a user keeps performing a first operation on the touch panel in a first predetermined duration or more and wherein the display screen displays respective concentric first and second areas in which the second area being disposed inside the first area forming a ring configuration with direction instruction patterns indicating bending direction therebetween and the processor directs the bending operation to be performed in the bending direction associated with a touch position in the first operation when the touch position is corresponding to the first area and wherein the processor being configured to stop the bending operation when the user swipes on the direction instruction patterns in the second area; and a code changing a speed of the bending operation of the bending portion according to an operation speed of the first operation.

15. An endoscope bending control method comprising:
preparing a display portion having a touch panel displaying a display screen;
displaying an endoscope image acquired by an endoscope on the display screen, the endoscope includes a bending portion configured to communicate with a bending driving portion and a bending control portion having codes of a bending control process to control the bending driving portion in accordance to instructions input via the touch panel; and
controlling the bending portion so as to perform a bending operation when a user keeps performing a first operation on the touch panel in a first predetermined duration or more and wherein the display screen displays respective concentric first and second areas in which the second area being disposed inside the first area forming a ring configuration with direction instruction patterns indicating bending direction therebetween and a processor directs the bending operation to be performed in the bending direction associated with a touch position in the first operation when the touch position is corresponding to the first area and wherein the processor being configured to stop the bending operation when the user swipes on the direction instruction patterns in the second area; and
changing a speed of the bending operation of the bending portion according to an operation speed of the first operation.

16. A touch panel device used in an endoscope device comprising:
a display portion having a display panel and a touch panel formed thereto and configured to display an endoscope image on the display panel acquired by an endoscope including a bending portion; and
a processor configured to control the bending portion so as to perform a bending operation when a user keeps performing a first operation on the touch panel in a first predetermined duration or more and wherein the display panel displays respective concentric first and second areas in which the second area being disposed inside the first area forming a ring configuration with direction instruction patterns indicating bending direction therebetween and the processor directs the bending operation to be performed in the bending direction associated with a touch position in the first operation when the touch position is corresponding to the first area and wherein the processor being configured to stop the bending operation when the user swipes on the direction instruction patterns in the second area;
wherein the processor reduces a speed of the bending operation when the user performs the first operation in a direction opposite to the bending direction of the bending portion.

17. A computer program product in a form of recording medium, used in a touch panel device, including a non-transitory computer readable medium having a bending control program code encoded thereon that when executed by a processor of a computer, the bending control program causes the computer to execute:
a code displaying, on a display portion having a display screen and a touch panel formed thereto, the display screen includes an endoscope image acquired by an endoscope having a bending portion;
a code controls the bending portion so as to perform a bending operation when a user keeps performing a first operation on the touch panel in a first predetermined duration or more and wherein the display screen displays respective concentric first and second areas in which the second area being disposed inside the first area forming a ring configuration with direction instruction patterns indicating bending direction therebetween and the processor directs the bending operation to be performed in the bending direction associated with a touch position in the first operation when the touch position is corresponding to the first area and wherein the processor being configured to stop the bending operation when the user swipes on the direction instruction patterns in the second area; and
a code reducing a speed of the bending operation when the user performs the first operation in a direction opposite to the bending direction of the bending portion.

18. An endoscope bending control method comprising:
preparing a display portion having a touch panel displaying a display screen;
displaying an endoscope image acquired by an endoscope on the display screen, the endoscope includes a bending portion configured to communicate with a bending driving portion and a bending control portion having codes of a bending control process to control the bending driving portion in accordance to instructions input via the touch panel; and
controlling the bending portion so as to perform a bending operation when a user keeps performing a first operation on the touch panel in a first predetermined duration or more and wherein the display screen displays respective concentric first and second areas in which the second area being disposed inside the first area forming a ring configuration with direction instruction patterns indicating bending direction therebetween and a processor directs the bending operation to be performed in the bending direction associated with a touch position in the first operation when the touch position is corresponding to the first area and wherein the processor being configured to stop the bending operation when the user swipes on the direction instruction patterns in the second area; and
reducing a speed of the bending operation when the user performs the first operation in a direction opposite to the bending direction of the bending portion.

* * * * *